United States Patent [19]

Kobayashi

[11] Patent Number: 5,023,124
[45] Date of Patent: Jun. 11, 1991

[54] ABSORBENT ARTICLE

[75] Inventor: Takatoshi Kobayashi, Tochigi, Japan

[73] Assignee: Kao Corporation, Tokyo, Japan

[21] Appl. No.: 570,451

[22] Filed: Aug. 21, 1990

[30] Foreign Application Priority Data

Aug. 21, 1989 [JP] Japan ................................ 1-97214[U]

[51] Int. Cl.⁵ ................................................ B32B 3/26
[52] U.S. Cl. ...................................... 428/76; 428/138;
428/304.4; 428/316.6; 428/913
[58] Field of Search ..................... 428/71, 74, 76, 137,
428/138, 304.4, 316.6, 913

[56] References Cited

U.S. PATENT DOCUMENTS 4,755,413  7/1988  Morris ................................. 428/138
4,806,408  2/1989  Pierre et al. .......................... 428/76
4,888,231  12/1989 Angstadt ............................... 428/76

Primary Examiner—William J. Van Balen
Attorney, Agent, or Firm—Sughrue, Mion, Zinn, Macpeak & Seas

[57] ABSTRACT

An absorbent article comprising a surface material, a liquid-impermeable backing material and an absorbent located therebetween, wherein said surface material comprises a liquid-retentive structure body with a three-dimensional skeleton structure having an average interskeleton distance of from 150 to 700 μm and a hydrophobic film being integrally provided with the liquid-retentive structure body so as to form a skin-contact face, and have openings penetrating through the liquid-retentive structure body and the hydrophobic film is disclosed. An absorbent article comprising an absorbent and the above-mentioned surface material is also disclosed. The absorbent article of the present invention may be processed into, for example, a sanitary napkin which can rapidly introduce a liquid into the absorbent via the openings, shows no turn back of the absorbed liquid toward the body even under the application of pressure, gives an excellent feel at use, maintains a dryness on the surface and can completely inhibit leakage of the liquid.

18 Claims, 2 Drawing Sheets

ABSORBENT ARTICLE

FIELD OF THE INVENTION

The present invention relates to an absorbent article. More particularly, it relates to an absorbent article such as a sanitary napkin which gives an improved feel at the use and has an excellent leakproof effect.

BACKGROUND OF THE INVENTION

The basic structure of a common absorbent article such as a sanitary napkin consists of a liquid-permeable surface material, a liquid-impermeable backing material and an absorbent located therebetween. Such an absorbent article has formed into a substantially rectangle shape. It is intensely required that such an absorbent article has an excellent absorption performance and a high leakproof effect showing no leak in any case. It is furthermore required that a liquid absorbed by the absorbent would never turn back and the absorbent article gives no unpleasant feel (for example, stickiness, physical disorder) at use.

Accordingly, attempts have been made to improve the absorption performance and liquid-retentive properties of absorbents used in absorbent articles such as sanitary napkin by, for example, incorporating a high absorbing polymer, providing an elastic material so as to suppress deformation or using a surface material capable of improving liquid-permeability into the absorbent or suppressing the turn back of a liquid. However, none of these attempts has achieved satisfactory results so far. This is proved by the fact that most of consumers' complaints concentrate upon leak, stickiness and unpleasant feel.

Recently, it has proposed to use as a surface material a nonwoven fabric comprising a large amount of hydrophobic fiber or a hydrophobic film provided with openings. Thus absorbent articles including sanitary napkins wherein these surface materials are used have been marketed. Although the hydrophobic materials used in these products suppress wetness and stickiness, they are poor in absorptivity and thus cause leakage. When large openings are provided in order to improve the absorptivity, the absorbed liquid is liable to turn back, which causes stickiness. Thus these products seemingly fail to satisfy both of these requirements contrary to each other.

SUMMARY OF THE INVENTION

In order to solve the above-mentioned problems, we have conducted extensive studies. As a result, we have found that an absorbent article, which comprises, as a surface material, a liquid-retentive structure body with a three-dimensional skeleton structure having an average interskeleton distance of from 150 to 700 μm and a hydrophobic film being integrally provided with the liquid-retentive structure body so as to form a skin-contact face, and have openings penetrating through the liquid-retentive structure body and the hydrophobic film, can rapidly introduce a liquid into said absorbent via the openings penetrating the liquid-retentive body and the hydrophobic film, shows no turn back of the absorbed liquid toward the body even under the application of pressure, gives an excellent feel at the use, maintains a dryness on the surface and can completely inhibit leakage of the liquid, thus completing the present invention.

Accordingly, the present invention provides an absorbent article comprising:
a surface material;
a liquid-impermeable backing material; and
an absorbent being located between said surface material and said liquid-impermeable backing material, wherein said surface material comprises:
(A) a liquid-retentive structure body with a three-dimensional skeleton structure having an average interskeleton distance of from 150 to 700 μm;
(B) a hydrophobic film being integrally provided with said liquid-retentive structure body so as to form a skin-contact face; and
(C) openings penetrating through said liquid-retentive structure body and said hydrophobic film.

The present invention further provides an absorbent article comprising:
an absorbent; and
a surface material being wound around the absorbent; wherein said surface material comprises:
(A) a liquid-retentive structure body with a three-dimensional skeleton structure having an average interskeleton distance of from 150 to 700 μm;
(B) a hydrophobic film being integrally provided with said liquid-retentive structure body so as to form a skin-contact face; and
(C) openings penetrating through said liquid retentive-structure body and said hydrophobic film.

1: surface material;
2: liquid-retentive structure body with three-dimensional skeleton structure;
3: hydrophobic resin film;
4: concave;
5: opening;
6: absorbent;
7: backing material;
8,9: sanitary napkin;
10 sample solution;
11: measurement table;
12: buret;
13: test piece;
14: load; and
15: glass filter.

DETAILED DESCRIPTION OF THE INVENTION

Now examples of the present invention will be described in detail by reference to the accompanying drawings, though the present invention is not restricted to these examples.

Figure 1:
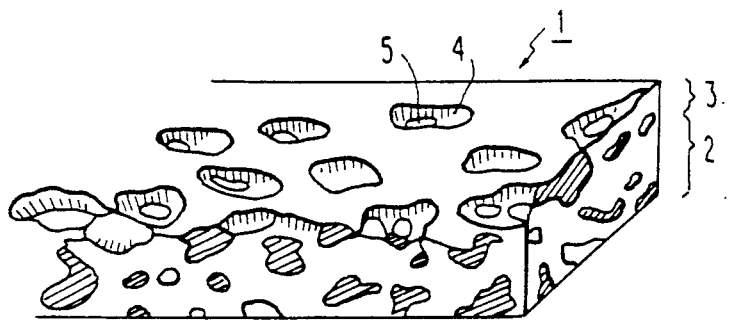
FIG. 1 is a schematic perspective section of an embodiment of the surface material to be used in the absorbent article of the present invention.
Figure 2:
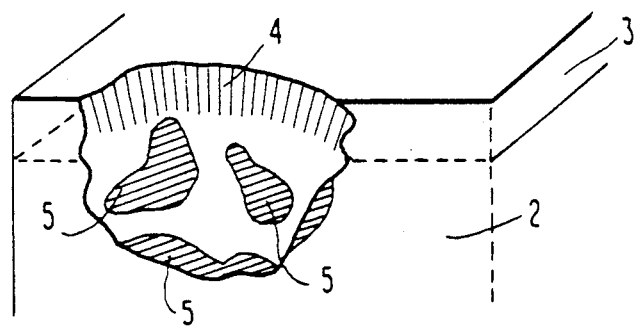
FIG. 2 is an enlarged section of an opening shown in FIG. 1.
Figure 3:
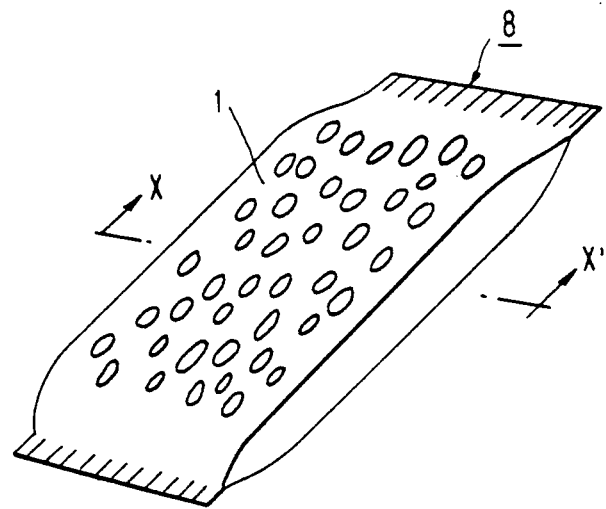
FIG. 3 is a schematic perspective section of a sanitary napkin with the use of the surface material which is an embodiment of the absorbent article of the present invention.
Figure 4:
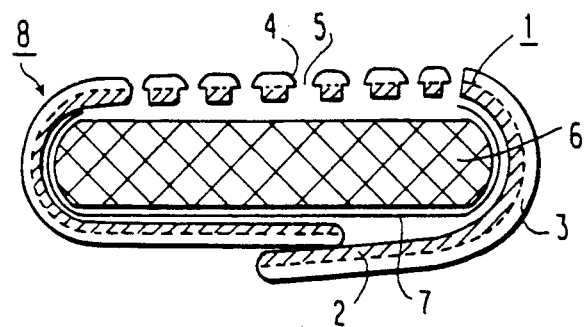
FIG. 4 is a cross section of the sanitary napkin of FIG. 3 taken along line X—X'.
Figure 5:
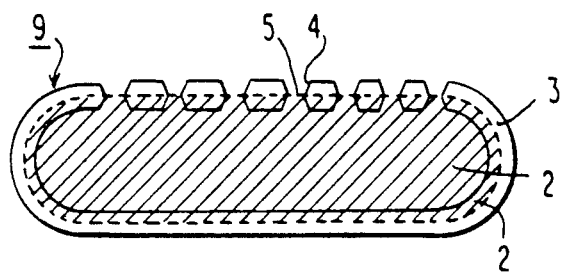
FIG. 5 is a section of a sanitary napkin which shows another embodiment of the absorbent article of the present invention.

FIG. 1 is a schematic perspective section of an embodiment of the surface material to be used in the absorbent article of the present invention. FIG. 2 is an enlarged section of openings shown in FIG. 1. FIG. 3 is a schematic perspective section of a sanitary napkin with the use of the surface material which is an embodiment of the absorbent article of the present invention. FIG. 4 is a cross section of the sanitary napkin of FIG. 3 taken along line X—X'. FIG. 5 is a section of a sanitary napkin which shows another embodiment of the absorbent article of the present invention.

As FIG. 1 shows, the surface material 1 comprises a liquid-retentive structure body 2 having a hydrophilic surface and a three-dimensional skeleton structure and a hydrophobic resin film 3 which is integrally provided with the structure body 2. The film 3 is provided plural concaves 4, which are distributed at random, each having an opening 5 penetrating through an cell in the structure 2 to elevate the absorption rate.

The liquid-retentive structure body with a three-dimensional skeleton structure to be used in the present invention may be made of any material without restriction, so long as it has an average interskeleton distance of from 150 to 700 μm. For example, it may be made of a porous material comprising a synthetic polymer such as polyurethane, polystyrene, polyethylene, polyester, polyvinyl alcohol, butadiene-styrene rubber (SBR) or nitrile-butadiene rubber; a porous material comprising a polysaccharide such as cellulose; a porous material comprising an inorganic material such as diatomaceous earth; and a porous material obtained by thermally welding or adhering with an adhesive synthetic fibers such as polyethylene (PE), polypropylene (PP) or polyethylene terephthalate (PET). Among these materials, porous materials comprising synthetic polymers, in particular, expanded products of polyurethane or polyolefin are preferable. It is still preferable to use a water-absorptive polyurethane expanded product (in which ethylene oxide amounts 20% by weight or more based on the total epoxides in polyols) which is obtained by a process described in Japanese Patent Application No. 63-294315, since this material can impart desirable hydrophilic properties, skeleton structure and compression stress relatively easily.

In the present invention, the term "average interskeleton distance" means an average diameter of cells determined by a method which will be described hereinafter in the case of an expanded product, or an average distance between adjacent fibers in the case of a porous material consisting of fibers. When a structure of an average interskeleton distance ranging from 150 to 700 μm is used, a liquid-retentive structure body excellent in liquid-absorption and liquid-retentive properties can be achieved.

When the average interskeleton distance is shorter than 150 μm, the absorption ratio becomes insufficient for a practical use. When it exceeds 700 μm, on the other hand, the liquid-retentive properties of the structure become insufficient. Thus the objects of the present invention cannot be achieved in these cases.

When the liquid-retentive structure body of the present invention is an expanded product, closed cells may be present in the three-dimensional structure together with open cells, though open cell are preferable to achieve a higher absorption performance. It is further preferable to use an expanded product having an open cell rate (determined by a method which will be described hereinafter) of 40% or above.

Cells separated from each other via cell film are called "closed cells". In contrast thereto, continuous cells which are not separated from each other (i.e., cells continuously connected each other through penetrating pores so as to penetrate the expanded product) are called "open cells". The term "cell film" means a film extending from a skeleton structure and having substantially the same composition as that of the skeleton.

Since the average cell diameter of the expanded product corresponds to the aforementioned interskeleton distance, it should range from 150 to 700 μm.

When the absorption rate is taken into consideration, the average pore diameter of the penetrating pores connecting cells (determined by a method which will be described hereinafter) may preferably range from 20 to 200 μm, more preferably from 60 to 100 μm.

As the elasticity of the liquid-retentive structure of the present invention, the compression stress at 50 % deformation (determined by a method which will be described hereinafter) may preferably range from 10 to 200 g/cm$^2$.

It is preferable that at least the surface of the skeleton structure of the liquid-retentive structure of the present invention is hydrophilic in a certain extent. When the skeleton is made of a hydrophobic material, it is preferable to treat the surface of the skeleton with an appropriate wetting agent to thereby impart the hydrophilic properties to the surface. When it is made of a material which is hydrophilic per se in a certain extent, it is unnecessary to treat it with any wetting agent. The latter case is preferable from the viewpoint of labor-saving. The hydrophilic properties may be numerically expressed with the use of a hydrophilicity rate determined by the powder method which will be described hereinafter. The hydrophilicity rate of the surface of the skeleton structure may be preferably 0.3 or above.

Determination method (1) Determination of average cell size, open cell rate and average penetrating pore diameter A test sample is photographed under an electron microscope and an area of each cell was measured with the use of an image analyzer (Avio EXCEL, trade name, manufactured by Nippon Avionics). Then the diameter of the circle corresponding to the area is referred to as the cell size. An average of 200 cells is referred to as the average cell size.

The open cell rate ($\alpha$) is determined in accordance with the following equation (1):

$$\text{Open cell rate } \alpha \, (\%) = \frac{N_0}{N_0 + N_1} \times 100 \quad (1)$$

where $N_0$ represents a number of penetrating pores connecting cells; and $N_1$ represents a number of the cell film without penetrating by the penetrating pore.

The open cell rate is determined by using data of $N_0 + N_1 = 200$.

Similarly, the average penetrating pore diameter is determined by measuring an area of each pore connecting cells and the diameter of the circle corresponding to the area is referred to as the pore diameter. With referring the pore diameter of a closed pore (closed cell) to 0, an average of 200 pores is referred to as the average penetrating pore size.

(2) Determination of 50% compression stress

A sample (100 mm×50 mm, 5 mm in thickness) is compressed with a tension compressor at a compression rate of 10 mm/min and a compression area of 10 cm². When the thickness of the sample reaches 50% of the initial thickness (i.e., the thickness of the sample reaches 2.5 mm), the compression stress per unit area is referred to as 50% compression stress (g/cm²).

(3) Determination of hydrophilicity rate

Figure 6:
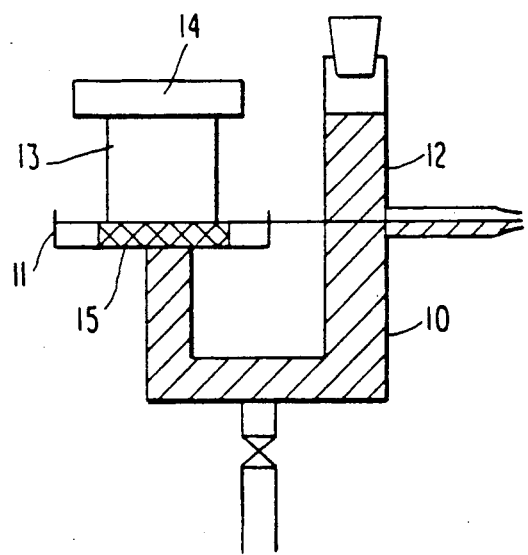
FIG. 6 is a section of a device employed for the determination of hydrophilicity rate.

The hydrophilicity rate is determined by using a device shown in FIG. 6.

First, the following procedure is conducted with use of ethanol (EtOH) as a sample solution 10.

A measurement table 11 is located at an even level with the liquid surface of the ethanol in a side opening of a buret 12 so as to equalize the pressure. A test piece (40mm×40 mm and 50 mm in thickness) is placed on a glass filter 15 (No. 1) of 80 mm in diameter located in the measurement table 11. Immediately, a load 14 (weight: 80 g, loading pressure: 5 g/cm²) was applied thereon and allowed to stand for 60 minutes. During this period, the ethanol absorbed by the test piece is compensated with air fed from the side opening of the buret so as to maintain the liquid surface at the even level. The amount of the ethanol absorbed during this period was determined.

Next, a sample solution 10 is changed into physiological saline solution and the amount of the absorbed physiological saline solution is determined by the same manner as the one described above. Then the hydrophilicity rate $\cos \theta$ ($\theta$: contact angle of physiological saline solution to test piece) of the test piece with physiological saline solution is calculated in accordance with the following equation.

This determination method of the hydrophilicity rate $\cos \theta$ is called the powder method.

$$\cos \theta = \frac{V_2 \times \gamma_1 \times \rho_2}{V_1 \times \gamma_2 \times \rho_2}$$

where $V_1$ represents an amount of EtOH absorbed after 60 min. (ml);

$V_1$ represents the surface tension of EtOH (dyn/cm);

$\rho_1$ represents the density of EtOH (g/cm³);

$V_2$ represents an amount of physiological saline solution absorbed after 60 min. (ml);

$\gamma_2$ represents the surface tension of physiological saline solution (dyn/cm); and $\rho_2$ represents density of physiological saline solution (g/cm³).

The surface material of the present invention is prepared by integrally incorporating a hydrophobic resin film to a liquid-retentive structure body having the above-mentioned three-dimensional skeleton structure and providing openings penetrating through the structure body and the hydrophobic film. As the hydrophobic resin to be used as the hydrophobic film, any one may be used so long as it can be formulated into a film. However it is preferable to use a resin capable of laminating, from the viewpoint of integrally incorporating to the structure body of the three-dimensional skeleton structure and providing openings. It is further preferable to use polyethylene and copolymers thereof therefor. After the lamination, the concaves 4 and penetrating openings 5, which are distributed at random, may be easily formed by a known manner, for example, suction or hot-air blowing. The size of the concave 4 may be determined depending on the surface conditions of the liquid-retentive structure body 2 of the three-dimensional skeleton structure. From the viewpoints of appearance and feel at use, the concave size (diameter) may preferably range from 1 to 5 mm. The openings 5 are present within the concave 4 at random and the diameter thereof is almost the same as the interskeleton distance of the liquid-retentive structure 2.

A sanitary napkin 8 shown in FIGS. 3 and 4, wherein the surface material of FIG. 1 is used, comprises a surface material 1, a backing material 7 comprising an extremely thin synthetic resin film such as polyethylene or a waterproof paper obtained by laminating such film onto paper, and an absorbent 6 comprising a split pulp or a high absorbing polymer which is located between the materials 1 and 7. This sanitary napkin is formed into a substantially rectangle shape.

In the sanitary napkin 8, openings are exclusively provided at the absorbing face of the surface material 1 while each of the sides and back face thereof (nonabsorbing faces) are merely a laminate without opening. The surface material 1 is wound around the absorbent 6 and the backing material 7 to form the sanitary napkin 8.

In the sanitary napkin 8, a liquid rapidly migrates into the absorbent 6 via penetrating openings 5 located in the concaves 4, and then the liquid is absorbed by the absorbent 6. When the liquid thus absorbed leaks from the absorbent 6 under applying of pressure, the three-dimensional structure body 2 prevents the liquid from leakage toward the body. Since the hydrophobic film 3 is hydrophobic as the whole and the penetrating openings 5 randomly distributed in the concaves 4 are integrated to the cells of the skeleton, each of the penetrating openings per se have a random orientation, the sanitary napkin suppresses the leakage of the liquid toward the body.

However the absorbent 6 may be deformed, the absorption performance of the sanitary napkin would be never changed, since the surface material 1 per se has an absorptivity and an elastic recovery. Thus the absorption performance of the sanitary napkin can remain unchanged. Therefore, the sanitary napkin of the present invention suffers from no leakage of blood and sustains a dry surface, which gives an excellent feel at use.

In the present invention, it is preferable to use an absorbent which is a liquid-retentive structure with a three-dimensional skeleton structure of which at least the surface is hydrophilic and an average interskeleton distance of from 50 to 700 μm. FIG. 5 shows embodiment of the present invention wherein such an absorbent is used. In a sanitary napkin 9 as shown in FIG. 5, no split pulp is used as an absorbent but a liquid-retentive structure body 2 having a three-dimensional skeleton structure per se serves as an absorbent, and the surface material is wound around the absorbent. Concaves 4 and penetrating openings 5 located therein are exclusively provided on the surface material at the absorbing face of the three-dimensional liquid-retentive structure 2 while each of the sides and back face (nonabsorbing face) thereof exclusively comprise a laminate without any opening. Thus it is expected that the sanitary napkin 9 of the present embodiment exerts the same effects as those achieved by the sanitary napkin 8.

The sanitary napkin 9, wherein the liquid-retentive structure body 2 of a three-dimensional skeleton structure is used as an absorbent, is largely advantageous for manufacturers, since the production process can be made simple.

The absorbent article of the present invention, which comprises a surface material comprising an elastic liquid-retentive structure body with a three-dimensional skeleton structure having open cells of a specific size and a hydrophobic resin film laminated thereonto, and provided with penetrating openings of random orientation, shows an enhanced liquid-penetration rate. Further, the surface material, which is hydrophobic and provided with openings of random orientation and has an elasticity, suffers from no leakage of a liquid toward the body. Therefore the stickiness of the absorbent face can be relieved and the leakage can be suppressed, thus giving an improved feel at use. Furthermore, the absorbent article of the present invention makes it possible to easily produce absorbent products such as sanitary napkins. Thus the absorbent article of the present invention is highly valuable in practice.

While the invention has been described in detail and with reference to specific examples thereof, it will be apparent to one skilled in the art that various changes and modifications can be made therein without departing from the spirit and scope thereof.

What is claimed is:

1. An absorbent article comprising:
a surface material;
a liquid-impermeable backing material; and
an absorbent being located between the surface material and the backing material, wherein the surface material comprises:
(A) a liquid-retentive structure body with a three-dimensional skeleton structure having an average interskeleton distance of from 150 to 700 $\mu$m;
(B) a hydrophobic film being integrally provided with said liquid-retentive body so as to form a skin-contact face; and
(C) openings penetrating through said liquid-retentive structure body and said hydrophobic film.

2. An absorbent article as claimed in claim 1, wherein said surface material has an absorbing face, sides and a back face, and said openings (C) are exclusively provided at the absorbing face.

3. An absorbent article as claimed in claim 2, wherein said hydrophobic film is provided concaves at the absorbing face and said openings are located in said concaves.

4. An absorbent article as claimed in claim 1, wherein said surface material is wound around the absorbent and the backing material.

5. An absorbent article as claimed in claim 1, wherein said liquid-retentive structure body has open cells and said open cells are connected each other through penetrating pores.

6. An absorbent article as claimed in claim 5, wherein an open cell rate of said liquid-retentive structure body is 40% or above.

7. An absorbent article as claimed in claim 5, wherein an average diameter of said penetrating pores is from 20 to 200 $\mu$m.

8. An absorbent article as claimed in claim 1, wherein a compression stress at 50% deformation of said liquid-retentive structure body is from 10 to 200 g/cm$^2$.

9. An absorbent article as claimed in claim 1, wherein the surface of said liquid-retentive structure body is hydrophilic.

10. An absorbent article comprising:
an absorbent; and
a surface material being wound around the absorbent; wherein said surface material comprises:
(A) a liquid-retentive structure body with a three-dimensional skeleton structure having an average interskeleton distance of from 150 to 700 $\mu$m;
(B) a hydrophobic film being integrally provided with said liquid-retentive structure body so as to form a skin-contact face; and
(C) openings penetrating through said liquid retentive-structure body and said hydrophobic film.

11. An absorbent article as claimed in claim 10, wherein said surface material has an absorbing face, sides and a back face, and said openings are exclusively provided at the absorbing face.

12. An absorbent article as claimed in claim 11, wherein said hydrophobic film is provided concaves at the absorbing face and said openings are located in said concaves.

13. An absorbent article as claimed in claim 10, wherein said liquid-retentive structure body has open cells and said open cells are connected each other through penetrating pores.

14. An absorbent article as claimed in claim 13, wherein an open cell rate of said liquid-retentive structure body is 40% or above.

15. An absorbent article as claimed in claim 13, wherein an average diameter of said penetrating pores is from 20 to 200 $\mu$m.

16. An absorbent article as claimed in claim 10, wherein a compression stress at 50% deformation of said liquid-retentive structure body is from 10 to 200 g/cm$^2$.

17. An absorbent article as claimed in claim 10, wherein said liquid-retentive structure body has hydrophilic surface.

18. An absorbent article as claimed in claim 10, wherein said absorbent is a liquid-retentive structure with a three-dimensional skeleton structure and have an average interskeleton structure of 50 to 700 $\mu$m.

* * * * *